United States Patent
Endlein et al.

(10) Patent No.: US 8,404,835 B2
(45) Date of Patent: Mar. 26, 2013

(54) METHOD FOR EXTRACTING D-GALACTOSE FROM VEGETABLE STARTING MATERIAL BY ACID HYDROLYSIS

(75) Inventors: Edgar Endlein, Wrestedt (DE); Nicolai Nagorny, Ammersbek (DE); Florian Repenn, Hamburg (DE)

(73) Assignees: Symrise AG, Holzminden (DE); Kaden Biochemicals GmbH, Hamburg (DE)

( * ) Notice: Subject to any disclaimer, the term of this patent is extended or adjusted under 35 U.S.C. 154(b) by 490 days.

(21) Appl. No.: 12/354,456

(22) Filed: Jan. 15, 2009

(65) Prior Publication Data

US 2009/0186146 A1   Jul. 23, 2009

(30) Foreign Application Priority Data

Jan. 18, 2008   (DE) .......................... 10 2008 000 101

(51) Int. Cl.
*C07H 1/08* (2006.01)
*C13K 13/00* (2006.01)

(52) U.S. Cl. ...................................................... 536/128

(58) Field of Classification Search .................. None
See application file for complete search history.

(56) References Cited

U.S. PATENT DOCUMENTS

| 1,718,837 | A | | 6/1929 | Schorger |
| 3,981,773 | A | | 9/1976 | Galzy et al. |
| 4,067,748 | A | | 1/1978 | Rowe et al. |
| 6,210,801 | B1 | * | 4/2001 | Luo et al. ....................... 428/393 |
| 6,987,183 | B2 | * | 1/2006 | Heikkila et al. .............. 536/124 |
| 7,157,431 | B2 | * | 1/2007 | McAnalley et al. ............ 514/23 |

FOREIGN PATENT DOCUMENTS

| EP | 0 168 127 | 1/1986 |
| EP | 0 499 164 | 8/1992 |
| EP | 1 046 719 | 10/2000 |
| EP | 1046719 | 10/2000 |
| GB | 2 407 573 | 5/2005 |
| WO | WO-2005/001145 | 1/2005 |
| WO | WO-2005/042788 | 5/2005 |

OTHER PUBLICATIONS

Willfor, S. et al., Wood Sci. Technol., "Isolation and Characterisation of water soluble polysaccharides from Norway spruce and Scots pine", 2004, vol. 38, pp. 173-179.*
S. Haq, G.A. Adams: "Structure of an arabinogalactan from tamarack (*Larix laricina*)" Can. J. Chem., Bd. 39, 1961, Seiten 1563-1573, XP002535922.
N. Banerji, A.K. Das: "A novel process for the preparation of pure D-galactose from green Bael-fruit (*Aegle marmelos*) gum" J. Inst. Chemists (India), Bd. 52, 1980, Seiten 57-58, XP008108116.
W. G. Campbell et al.: "The e-galactan of Larch Wood (*Larix decidua*)" J. Chem. Soc., 1948, Seiten 774-777, XP002535924 (Best available copy).
Extended European Search Report, European Application No. EP 09150559.4, received Jul. 23, 2009.

* cited by examiner

*Primary Examiner* — Eric S Olson
*Assistant Examiner* — Bahar Craigo
(74) *Attorney, Agent, or Firm* — Novak Druce Connolly Bove + Quigg LLP

(57) ABSTRACT

A description is provided of a method for extraction of D-galactose, with the following steps:
provision of an aqueous solution or suspension of galactoarabinan, wherein the aqueous solution or phase has a pH of less than or equal to 3;
heating of the solution or suspension to a temperature in the range from 80 to 160° C. and maintaining it at this temperature for a period in the range from 1 to 40 hours;
separation of the D-galactose formed, possibly in a mixture with other substances, from the resultant product mixture.

4 Claims, No Drawings

METHOD FOR EXTRACTING D-GALACTOSE FROM VEGETABLE STARTING MATERIAL BY ACID HYDROLYSIS

CROSS-REFERENCE TO RELATED APPLICATION

This application claims benefit of priority to DE 10 2008 000 101.5, filed on Jan. 18, 2008, which is incorporated herein by reference in its entirety. The present invention concerns a method for extracting (and purifying) galactose, in particular D-galactose ((+)-galactose, CAS-No: 59-23-4), from isolated vegetable starting material, in particular from arabinogalactan (INCI—Name: galactoarabinan, CAS-NO. 9036-66-2).

Galactose is important in enzymatic and biochemical research as a nutrient medium and as a synthesis module. Galactose is also widely used in the pharmaceuticals sector, both as a carrier and as an active substance. D-galactose is particularly important as a precursor for pharmaceutically active substances, as an active substance carrier or also as a chiral module in chemical synthesis.

Methods for the synthetic manufacture of D-galactose from the corresponding polyglycosides by acid hydrolysis are already known.

The extraction of D-galactose through hydrolysis of lactose has been described a number of times, see for example U.S. Pat. Nos. 3,981,773, 4,067,748, EP 0 168 127 or EP 0 499 164.

In the methods to date, in which galactose is synthesised from lactose on a large scale, there is always the problem of BSE-/TSE contamination, because the lactose used is of animal origin. Furthermore, products containing lactose are often undesirable since these are unsuitable for people desirous of kosher food or who have a lactose intolerance.

With galactose of a vegetable origin, however, it is possible to manufacture a product that is not contaminated by allergens such as, in particular, lactose.

So, there is great interest in production methods in which the said galactose can be manufactured with a high yield and purity from vegetable starting material.

To do this, EP 1 046 719 proposes the hydrolysis of oligosaccharide-containing legume compositions, as occurring, for example, in soya, rapeseed or sunflowers. Rare sugars, such as arabinose, should preferably not be a component here of the oligosaccharides to be hydrolysed in accordance with EP 1 046 719.

In Carbohydrate Research 2006 (341), 870-880 the non-catalytic release of galactose from galactomannan at temperatures of 180-240° C. and with a reaction time of 3-6 minutes is described. Galactoarabinan and hydrolysis thereof are not mentioned.

In Carbohydrate Research 1997 (301) 89-93 the acid hydrolysis of *Larix occidentalis* is described for determination of the monosaccharide composition. No details of industrial processes are provided.

In J. Inst. Chemists (India), Vol. 52, March, 1980, 57-58 and IN 158940 a process is described for the synthesis of galactose from the gum of the green fruit *Aegle marmelos*. Here to begin with, pure D-galactan is extracted from the gum by mild acid hydrolysis, which is then transformed by hydrolysis into D-galactose in the presence of a strong acid. Here the preference is hydrochloric and sulfuric acids, with the maximum yield of D-galactose with hydrochloric acid (5% by weight) being 25-30%, whereas with sulfuric acid (4% by weight) a yield of 50-55 % of D-galactose is achieved. Following neutralization with barium carbonate the filtrate is filtered through an acid and a basic ion exchanger and then concentrated. The syrup obtained in this way is absorbed in water and the D-galactose is brought to crystallization under cooling. According to paper chromatography, crystalline D-galactose is obtained with a purity of 99.5%. The production takes place on a laboratory scale.

In J. Chem. Soc. 1948, 774 $\epsilon$-galactan from *Larix decidua* and the hydrolysis and methylation of this are described. Initially the polysaccharide was heated with 0.01 N sulfuric acid for 40 hours at 90° C., the solution neutralized with barium carbonate and filtered. The filtrate was concentrated to form a syrup, which was fractionated from aqueous solution by addition of alcohol. The second fraction thereby obtained was further hydrolysed for 4 hours with boiling N-sulfuric acid, and this solution was likewise neutralized with barium carbonate, filtered and concentrated to form a syrup, which crystallized. Through trituration with alcohol crystalline D-galactose was obtained.

In J. Chem. Soc. 1953, 1672 the hydrolysis of $\epsilon$-galactan from larch with cold or hot hydrochloric acid is described, which is followed by filtration and neutralization with a basic ion exchanger. Here the filtrate was also concentrated and introduced into alcohol, whereupon the filtrate was separated from the precipitate and concentrated to form a syrup. The syrup obtained in this way was fractionated via a column of cellulose with a mixture of n-butanol and water, with eluation of first the L-arabinose and then the D-galactose.

In Chemistry and Industry 1952, 954 a description is given of how $\epsilon$-galactan from larch can be hydrolysed by means of hydrochloric acid, wherein the hydrolysis can take place with N-hydrochloric acid at 20° C. or with 0.01 N hydrochloric acid at 100° C. The saccharide mixture obtained in this way was fractionated on cellulose wherein disaccharides were isolated from L-arabinose units.

U.S. Pat. No. 1,718,837 describes how the carbohydrates from the larch *Larix occidentalis* can be converted by means of oxidation with nitric acid into mucic acid. The thermal treatment of an aqueous wood extract or of the wood itself in the presence of a small amount of a mineral acid resulted in the insolubility of the tannin present in the extract, wherein the galactan in the wood is to a certain extent hydrolysed into galactose and the galactose thereby serves as a starting material for the formation of mucic acid in accordance with U.S. Pat No. 1,718,837.

WO 2005/001145 concerns the extraction of D-galactose from vegetable material, wherein a chromatographic step on an ion exchanger is seen as essential there in order to obtain a fraction from which the D-galactose can then be extracted by means of crystallization. Galactoarabinan and the hydrolysis thereof are not mentioned in WO 2005/001145.

In GB 2 407 573 and WO 2005/042788 the extraction of arabinose from vegetable fibers is described, wherein as preferred vegetable materials gum arabic, ghatti gum and traganth gum are indicated.

Despite the abovementioned and other known methods for the release or extraction and purification of D-galactose from vegetable material there is also a need for an improved method which can be performed in particular on an industrial scale. Each of the previously known methods has at least one or more of the following disadvantages:

low productivity (low educt concentration, low yield, long reaction time), low purity, occurrence of undesired by-products (such as decomposition products of the plant matrix).

The primary task for the present invention, therefore, was to indicate a method for extracting D-galactose from vegetable starting material, which allows the use of high educt concentrations and at the same time leads to high product yields. In the method indicated it should preferably be possible to extract D-galactose with a high purity and which is as far as possible free from inorganic impurities, wherein preferably at most a low proportion of other sugars should be present.

The task set is solved by a method for extraction of D-galactose, with the following steps:
provision of an aqueous solution or suspension of galactoarabinan, wherein the aqueous solution or phase (of the suspension) has a pH of less than or equal to 3;
heating of the solution or suspension to a temperature in the range from 80 to 160° C. and maintaining it at this temperature for a period in the range from 1 to 40 hours (acid hydrolysis);
separation of the D-galactose formed, possibly in a mixture with other substances, from the resultant product mixture.

The present invention is based on extensive own investigations into the extraction by hydrolysis of D-galactose from natural biopolymers. These own investigations have shown that with the various biopolymers the hydrolysates obtained in each case were as a rule not suitable for extracting D-galactose on a large or industrial scale.

Ultimately, however, it turns out that the method according to the invention of extracting D-galactose from galactoarabinan (by acid hydrolysis) is also particularly suited to solving the task set.

The aqueous solution or suspension of galactoarabinan is, in a method according to the invention for extracting D-galactose, preferably provided by the following steps:
(i) provision of water;
(ii) dissolution or suspension of galactoarabinan in the water provided in step (i) or water acidified according to step (iii);
(iii) addition of a strong inorganic acid (preferably hydrochloric acid, see below) to the solution or suspension obtained in accordance with step (ii) or to the water provided in step (i),
so that the aqueous phase of the acidified solution or suspension has a pH of less than or equal to 3, preferably less than or equal to 2.

The aqueous solution or suspension of galactoarabinan provided in a method according to the invention, is in accordance therewith, manufactured according to a first alternative, in that galactoarabinan is dissolved or suspended in water and then a strong inorganic acid is added to this solution or suspension. The thereby acidified solution or suspension preferably has a pH of less than or equal to 2. According to a second alternative the aqueous solution or suspension of galactoarabinan described above is manufactured by the addition of a strong inorganic acid to water provided, so that the acidified water has a pH of less than or equal to 3, preferably less than or equal to 2, and then galactoarabinan is dissolved or suspended in the acidified water.

In accordance with the invention galactoarabinan from the larch (*Larix*), a naturally occurring polymer, is preferably used, which contains galactose and arabinose. Particularly suitable types of larch are *Larix occidentalis, Larix larcicina, Larix lyallii, Larix decidua, Larix dahurica, Larix leptolepis* and *Larix siberica*. Accordingly the galactoarabinan to be used according to the invention can be contaminated by other components originating from the larch.

In a preferred embodiment of the method according to the invention the galactoarabinan has an average molecular weight in the range from 2,000-250,000 Dalton, preferably an average molecular weight in the range from 5,000-100,000 Dalton and particularly preferably an average molecular weight in the range from 5,000-50,000 Dalton.

Commercially available galactoarabinans, which can be used in a method according to the invention, are available, inter alia, under the brand or product names Larex® UF, Lara Care® A 200, Cleartrac or FiberAid®, from Larex International or Lonza Group, for example.

The starting material selected according to the invention (e.g. galactoarabinan) and the reaction process selected according to the invention (in particular: pH; temperature; reaction time; acid used and $pK_a$ of the acid used) make possible a method that can be applied industrially, in which well crystallized D-galactose with a high purity is obtained. A particularly preferable embodiment is represented by a method according to the invention (as described above), in which the aqueous solution or suspension of galactoarabinan provided contains 1 to 35% by weight, preferably 5 to 25% by weight, galactoarabinan, relating to the total weight of the solution or suspension.

Particularly preferably a method according to the invention comprises, in particular in one of its preferred embodiments, the following step:
heating of the solution or suspension provided to a temperature in the range from 90 to 125° C. and maintaining it at this temperature for a period in the range from 10 to 30 hours.

In addition, a method according to the invention, preferably in an embodiment described above as preferable, comprises the following step:
neutralization of the solution or suspension that exists after heating and maintaining the temperature, preferably on one ion exchanger or more than one of these one after another.

Accordingly, the aqueous solution or phase is preferably neutralized on an ion exchanger or a plurality of these one after another. The neutralization preferably takes place on a basic and then an acid ion exchanger one after another or on a basic, an acid and then a basic ion exchanger again one after another.

In a method according to the invention the separation of the D-galactose formed (possibly in a mixture with other substances) from the resultant product mixture preferably takes place by crystallization. Accordingly, methods according to the invention comprising the following step are particularly preferred:
separation of the D-galactose formed, possibly in a mixture with other substances, from the resultant product mixture by crystallization.

Particularly preferred is an embodiment of a method according to the invention with the following steps:
provision of the aqueous solution or suspension of galactoarabinan by:
(i) provision of water;
(ii) dissolution or suspension of galactoarabinan in the water provided in step (i) or water acidified according to step (iii);
(iii) addition of a strong inorganic acid, preferably hydrochloric acid, to the solution or suspension obtained in accordance with step (ii) or to the water provided in step (i) (see above regarding the alternative sequence of the steps), so that the aqueous phase of the acidified solution or suspension has a pH of less than or equal to 3, preferably less than or equal to 2, so that the aqueous solution or suspension of galactoarabinan provided contains 1 to 35% by weight, preferably 5 to 25% by weight, galactoarabinan, relating to the total weight of the solution or suspension;
and then (iv) heating of the solution or suspension provided to a temperature in the range from 90 to 125° C. and maintaining it at this temperature for a period in the range from 10 to 30 hours;

(vi) neutralization of the solution or suspension that exists after heating and maintaining the temperature, preferably on one ion exchanger or more than one of these one after another;

(viii) separation of the D-galactose formed, possibly in a mixture with other substances, from the resultant product mixture, preferably by crystallization.

As already mentioned, a method in accordance with the invention is particularly well suited for extracting or providing D-galactose on an industrial scale. The method according to the invention is therefore preferably carried out on an industrial scale. Here, the term "industrial scale" in the context of the present invention means that a solution or suspension of galactoarabinan that exists in accordance with a method according to the invention has a volume of at least 100 liters.

In methods according to the invention for extracting D-galactose a strong inorganic acid is used for acidification. As already mentioned, this is preferably added to a solution or suspension obtained in accordance with step (ii) or to water provided in accordance with step (i), so that the acidified solution or the aqueous phase of the suspension has a pH of less than or equal to 3, preferably less than or equal to 2. For particularly preferable ranges of pH settings see below. "Strong" inorganic acids, in the context of the present invention are in particular inorganic acids, with a $pK_A$ of 2.2 or less. Particularly preferably, the strong inorganic acid is selected from the group consisting of: hydrochloric acid, sulfuric acid, phosphoric acid and mixtures thereof, wherein the best results have been achieved with hydrochloric acid and this is therefore particularly preferred in all embodiments of the method according to the invention.

Accordingly a particularly preferable embodiment of the present invention is a method according to the invention (as described above), wherein for the acidification a strong inorganic acid is used, which is selected from the group comprising hydrochloric acid, sulfuric acid, phosphoric acid and mixtures thereof, preferably hydrochloric acid.

According to a particularly preferred embodiment of the present invention a method according to the invention (as described above) comprises the following steps:

provision of the aqueous solution or suspension of galactoarabinan through:
(i) provision of water;
(ii) dissolution or suspension of galactoarabinan in the water provided in step (i) or water acidified in accordance with step (iii);
(iii) addition of hydrochloric acid (i.e the generally preferred acid) to the solution or suspension obtained in accordance with step (ii) or to the water provided in step (i),
so that the aqueous phase of the acidified solution or suspension has a pH in the range from 1 to 1.3,
so that the aqueous solution or suspension of galactoarabinan provided contains 5 to 25 % by weight of galactoarabinan, relating to the total weight of the solution or suspension;
(iv) heating of the solution or suspension provided to a temperature in the range from 95 to 110° C. and maintaining it at this temperature for a period in the range from 20 to 30 hours;
(v) preferably filtration (in particular when a suspension of galactoarabinan is being used);

(vi) neutralization of the solution or suspension that exists after heating and maintaining the temperature or after filtration, preferably one after another at least on a basic and an acid ion exchanger;

(vii) preferably stirring of the neutralized mixture with an ethanol-rich mixture of ethanol and water (flushing);

(viii) separation of the D-galactose formed, possibly in a mixture with other substances, from the resulting product mixture, preferably by crystallization;

(ix) recrystallization as necessary, preferably from water.

Filtration and/or flushing are also generally preferred in the method according to the invention.

Preferably a plurality or all of the preferred method embodiment features or parameters are contained in the present method according to the invention. Accordingly, a method according to the invention preferably contains all the described steps (i), (ii), (iii), (iv), (v), (vi), (vii), (viii) and (ix), preferably in each case in an embodiment designated above as being preferable.

In own investigations the best results were achieved with the use of hydrochloric acid for acidification in a method according to the invention, as already mentioned. The use of hydrochloric acid has proven to be particularly advantageous in the entire manufacturing process, in particular for the (acid) hydrolysis of the galactoarabinan, but also for provision of the aqueous solution or suspension of galactoarabinan (as described above). In addition the use of hydrochloric acid had an advantageous effect on steps (iii), (iv), (vi), (vii) and (viii) that are preferably contained in a method according to the invention. Further investigations showed that when sulfuric acid (37% by weight) is used instead of hydrochloric acid, in particular for the use in accordance with step (iii) of a method according to the invention, the process as a whole, but in particular the hydrolysis, the flushing and the crystallization, proved to be appreciably poorer or harder to perform. The best yields were achieved with hydrochloric acid.

In own investigations, as already mentioned, the best results were achieved when hydrochloric acid was used for acidification according to a method available according to the invention. The use of hydrochloric acid proved to be particularly advantageous for the manufacturing process as a whole, in particular for the (acid) hydrolysis of the galactoarabinan, but also for the provision of the aqueous solution or suspension of galactoarabinan (as described above). In addition, the use of hydrochloric acid had an advantageous effect on steps (iii), (iv), (vi), (vii) and (viii) preferably contained in a method according to the invention. Further investigations showed that when sulfuric acid (37% by weight) is used instead of hydrochloric acid, in particular for the use in accordance with step (iii) of a preferred method according to the invention, the process as a whole, but in particular the hydrolysis, the flushing and the crystallization, proved to be appreciably poorer or harder to perform.

The following Table describes the advantageous effects which in the context of own investigations it was possible to observe for a more detailed characterization of some steps that are preferably contained in a method according to the invention. The parameters and features of the reaction process described in the following as advantageous are particularly preferable for a method according to the invention, independently of one another and—preferably—in combination with each other.

| Method step | Effect |
| --- | --- |
| Hydrolysis | Use of hydrochloric acid particularly preferable, with sulfuric acid the hydrolysis is more incomplete and more impure.<br>pH = 1-1.3 preferably, since at high pH the reaction is still incomplete after 24 hours; in an even stronger acid medium decomposition of the D-galactose takes place.<br>The dilution of the acid indicated is advantageous since at a higher concentration complete hydrolysis does not take place. |
| Filtration | Filtration keeps back the insoluble components which otherwise could hinder any crystallization being performed. |
| Neutralization | Without neutralization the pH may drop too far in any concentration, so that the D-galactose (in part) would be destroyed.<br>Advantageously when neutralization takes place via an ion exchanger filtration takes place simultaneously. |
| Flushing (mixing with an ethanol-rich mixture of ethanol and water) | In this way, secondary components such as arabinose, galacturonic acid and/or polymer residues are to some extent dissolved out.<br>Preferably, subsequent crystallizations are more successful because the starting material is in a purer form. |
| Concentration | A reduction in the water quantity is advantageous, so that the raw ingredient can be crystallized more easily. |
| Recrystallization | This allows a purification of the product to a 98% product, with the crystallization preferably taking place from water, wherein the crystallization of the D-galactose is preferably initiated by the addition of ethanol. |

Accordingly a preferred method according to the invention preferably comprises the additional step of:
reduction of the water quantity (preferably concentration by distillation) in the (if necessary filtered and if necessary neutralized) solution or suspension existing following heating and maintaining the temperature (concentration).

Flushing has proven to be a particularly preferable step in a method according to the invention. Flushing means the dissolving out of secondary components from the raw D-galactose by stirring with an ethanol-rich mixture of ethanol and water, wherein in these mixtures the ethanol content preferably is in the range from 75-98% by weight, more preferably in the range from 80-95% by weight. By flushing a purity of D-galactose following crystallization of 98% or more is achieved.

The D-galactose obtained in accordance with the method according to the invention has a high purity, is easy to crystallize and has a characteristic fingerprint.

A further aspect of the present invention thus concerns a mixture comprising D-galactose, which can be manufactured in accordance with a method according to the invention (as described above), preferably in an embodiment designated above as preferable.

A further aspect of the present invention concerns a mixture comprising D-galactose (preferably as described above), comprising or consisting of the following components:
Galacturonic acid: at up to 1% by weight, preferably 0.2-1% by weight,
L-arabinose: at up to 1.5% by weight, preferably 0.3-1.5% by weight,
D-galactose: 97.5-99.5% by weight. The percentage weight figures relate here to the total dry mass of the mixture.

Preferably, a mixture according to the invention like that described above preferably comprising the D-galactose has a maximum residual moisture of 0.5% by weight, preferably a maximum of 0.3% by weight.

For the purposes of the present invention and the task to be solved, in the method according to the invention galactoarabinose from vegetable starting material is used. Accordingly, a mixture according to the invention, containing D-galactose, is preferably lactose-free.

A method according to the invention (as described above) for extracting D-galactose and for the manufacture of a mixture according to the invention comprising D-galactose (as described above) is carried out in a preferred example as follows:

500 kg of galactoarabinan (e.g. FiberAid®) are dissolved or suspended in 4,000-5,000 l of water. The pH is adjusted using approximately 50-60 l hydrochloric acid (30% by weight) to a value in the range from 1.0-1.5. The temperature is adjusted to 100° C. The hydrolysis is carried out for 24 hours (hydrolysis control by means of HPLC). Once the hydrolysis is complete cooling takes place to 50-60° C., with filtration (for example by means of a chamber filter press, for example with the Hyflo filter aid) and neutralization, with the solution or the suspension being passed over an alkaline ion exchanger and then again over an acid ion exchanger and then again over an alkaline ion exchanger. The ion exchangers are rinsed with approximately 2,000 l town water. Then the solution or suspension is concentrated by distillation (to approximately 1,500 l) and made to crystallize. The raw ingredient is centrifuged. 500 l 90% by weight of ethanol (remainder: water) are added to the raw product and agitated for one hour at a temperature of approximately 20° C. Through filtration (for example in a chamber filter press) the flushing liquor is separated from the solid matter. This process is carried out twice. The D-galactose raw product is dissolved for recrystallization (100° C., water, saturated solution), active charcoal is added and then filtration performed, for example via the Hyflo filter aid. From the filtrate the D-galactose can be crystallized again and then centrifuged. If necessary, for further purification, recrystallization can be performed again (saturated solution crystallization). Next, the D-galactose obtained in this way is dried (for example by circulating air or vacuum drying cabinet) and ground to the desired particle size.

Further aspects of the present invention emerge from the examples and the attached claims.

In the following the invention is explained in more detail using examples. Unless otherwise stated, all figures relate to the weight.

EXAMPLE

Extraction of D-galactose from Galactoarabinan 55 kg of hydrochloric acid (30% by weight) are placed in 4,500 l (town) water and heated to 80° C. In the resulting acid solution 500 kg galactoarabinan (Lara Care A® 200) are introduced under agitation and the suspension or solution obtained is heated to 100° C. After 24 hours' reaction time at 100° C. the reaction mixture is cooled to approximately 60° C. and filtered. Then, the reaction mixture is concentrated by evaporation and an initial crystallization is performed. Following centrifugation of the crystals these are if necessary recrystallized one or more times from water, centrifuged, dried and ground to the desired particle size.

The dried and homogenized solid matter was analyzed by HPLC. Typically a purity of greater than or equal to 97% was achieved.

HPLC chromatography conditions:
Column: Varian MetaCarb 87C
Temperature: 75° C.

Flow: 0.5 l/min
Eluent: HPLC water
Detection: Refraction index
Galacturonic acid (retention time 10-12 min.): up to 1% by weight
L-Arabinose (retention time 15-17 min.): up to 1.5% by weight
D-galactose (retention time 13-15 min.): 97.5-99% by weight Specific Embodiments:

Specific embodiment one comprises a method for extraction of D-galactose, with the following steps:
 provision of an aqueous solution or suspension of galactoarabinan, wherein the aqueous solution or phase has a pH of less than or equal to 3;
 heating of the solution or suspension to a temperature in the range from 80 to 160° C. and maintaining it at this temperature for a period in the range from 1 to 40 hours;
 separation of the D-galactose formed, possibly in a mixture with other substances, from the resultant product mixture.

Specific embodiment two comprises the method as in specific embodiment one, with the following steps:
 provision of the aqueous solution or suspension of galactoarabinan by:
 (i) provision of water;
 (ii) dissolution or suspension of galactoarabinan in the water provided in step (i) or water acidified according to step (iii);
 (iii) addition of a strong inorganic acid to the solution or suspension obtained in accordance with step (ii) or the water provided in step (i),
 so that the aqueous phase of the acidified solution or suspension has a pH of less than or equal to 3, preferably less than or equal to 2.

Specific embodiment three comprises the method as in specific embodiments one or two, wherein the galactoarabinan has an average molecular weight in the range from 2,000-250,000 Dalton, preferably an average molecular weight in the range from 5,000-100,000 Dalton and particularly preferably an average molecular weight in the range from 5,000-50,000 Dalton.

Specific embodiment four comprises the method as in any one of the preceding specific embodiments, wherein the aqueous solution or suspension of galactoarabinan provided contains 1 to 35% by weight, preferably 5 to 25% by weight galactoarabinan, relating to the total weight of the solution or suspension.

Specific embodiment five comprises the method as in any one of the preceding specific embodiments with the following step:
 heating of the solution or suspension to a temperature in the range from 90 to 125° C. and maintaining it at this temperature for a period in the range from 10 to 30 hours.

Specific embodiment six comprises the method as in any one of the preceding specific embodiments with the following step:
 neutralization of the solution or suspension that exists after heating and maintaining the temperature, preferably on one ion exchanger or more than one of these one after another.

Specific embodiment seven comprises the method as in any one of the preceding specific embodiments with the following step:
 separation of the D-galactose formed, possibly in a mixture with other substances, from the resultant product mixture by crystallization.

Specific embodiment eight comprises the method as in any one of the preceding specific embodiments, with the following steps:
 provision of the aqueous solution or suspension of galactoarabinan by:
 (i) provision of water;
 (ii) dissolution or suspension of galactoarabinan in the water provided in step (i) or water acidified according to step (iii),
 (iii) addition of a strong inorganic acid, preferably hydrochloric acid, to the solution or suspension obtained in accordance with step (ii) or to the water provided in step (i),
 so that the aqueous phase of the acidified solution or suspension has a pH of less than or equal to 3, preferably less than or equal to 2,
 so that the aqueous solution or suspension of galactoarabinan then contains 1 to 35% by weight, preferably 5 to 25% by weight galactoarabinan, relating to the total weight of the solution or suspension;
 and then:
 (iv) heating of the solution or suspension provided to a temperature in the range from 90 to 125° C. and maintaining it at this temperature for a period in the range from 10 to 30 hours;
 (vi) neutralization of the solution or suspension that exists after heating and maintaining the temperature, preferably on one ion exchanger or more than one of these one after another;
 (viii) separation of the D-galactose formed, possibly in a mixture with other substances, from the resultant product mixture, preferably by crystallization.

Specific embodiment nine comprises the method as in any one of the preceding specific embodiments, wherein for acidification a strong inorganic acid is used, selected from the group comprising: hydrochloric acid, sulfuric acid, phosphoric acid and mixtures thereof, preferably hydrochloric acid.

Specific embodiment ten comprises the method as in any one of the preceding specific embodiments, with the following steps:
 provision of the aqueous solution or suspension of galactoarabinan by:
 (i) provision of water;
 (ii) dissolution or suspension of galactoarabinan in the water provided in step (i) or water acidified in accordance with step (iii);
 (iii) addition of hydrochloric acid to the solution or suspension obtained in accordance with step (ii) or to the water provided in step (i),
 so that the aqueous phase of the acidified solution or suspension has a pH in the range from 1 to 1.3,
 so that the aqueous solution or suspension of galactoarabinan provided contains 5 to 25% by weight of galactoarabinan, relating to the total weight of the solution or suspension;
 and then:
 (iv) heating of the solution or suspension provided to a temperature in the range from 95 to 110° C. and maintaining it at this temperature for a period in the range from 20 to 30 hours;
 (v) preferably filtration;
 (vi) neutralization of the solution or suspension that exists after heating and maintaining the temperature or after filtration, preferably one after another on at least a basic and an acid ion exchanger;
 (vii) preferably stirring of the neutralized mixture with an ethanol-rich mixture of ethanol and water (flushing);
 (viii) separation of the D-galactose formed, possibly in a mixture with other substances, from the resultant product mixture, preferably by crystallization;
 (ix) recrystallization as necessary, preferably from water.

Specific embodiment eleven comprises a mixture containing D-galactose, which can be produced according to a method as in any one of the preceding specific embodiments.

Specific embodiment twelve comprises the mixture containing D-galactose, preferably as in specific embodiment eleven, comprising or consisting of:

Galacturonic acid: at up to 1% by weight, preferably 0.2-1% by weight,

L-arabinose: at up to 1.5% by weight, preferably 0.3-1.5% by weight,

D-galactose: 97.5-99.5% by weight wherein the percentage weight figures relate to the total dry mass of the mixture.

Specific embodiment thirteen comprises the mixture as in specific embodiment eleven or twelve, with residual moisture of a maximum of 0.5% by weight, preferably a maximum of 0.3% by weight.

The invention claimed is:

1. A D-galactose mixture produced according to the process comprising:
   (i) providing water;
   (ii) dissolving or suspending galactoarabinan in the water provided in (i) or water acidified in accordance with (iii);
   (iii) adding hydrochloric acid to the solution or suspension obtained in accordance with (ii) or to the water provided in (i), so that the aqueous phase of the acidified solution or suspension has a pH in the range from 1 to 1.3, so that the aqueous solution or suspension of galactoarabinan provided contains 5 to 25% by weight of galactoarabinan, relating to the total weight of the solution or suspension;
   and then:
   (iv) heating of the solution or suspension provided to a temperature in the range from 95 to 110° C. and maintaining it at this temperature for a period in the range from 20 to 30 hours;
   (v) optionally filtering the solution or suspension;
   (vi) neutralizing the solution or suspension that exists after heating and maintaining the temperature or after filtration;
   (vii) separating the D-galactose formed, possibly in a mixture with other substances, from the resultant product mixture; and
   (viii) recrystallizing the D-galactose as necessary,
   and wherein the D-galactose mixture comprises:
   Galacturonic acid: at 0.2-1% by weight,
   L-arabinose: at up to 1.5% by weight,
   D-galactose: at 97.5-99.5% by weight,
   wherein the percentage weight figures relate to the total dry mass of the mixture.

2. The mixture as claimed in claim 1, further comprising a maximum residual moisture of 0.5% by weight.

3. A D-galactose mixture, comprising:
   Galacturonic acid: at 0.2 to 1% by weight,
   L-arabinose: at 0.3% to 1.5% by weight,
   D-galactose: 97.5-99.5% by weight,
   wherein the percentage weight figures relate to the total dry mass of the mixture.

4. The mixture of claim 2, wherein the maximum residual moisture is 0.3% by weight.

* * * * *